United States Patent [19]

Yabe

[11] Patent Number: 4,667,656
[45] Date of Patent: May 26, 1987

[54] ENDOSCOPE APPARATUS HAVING NOZZLE ANGULARLY POSITIONED IMAGE SENSOR

[75] Inventor: Hisao Yabe, Hachioji, Japan

[73] Assignee: Olympus Optical Co., Ltd., Tokyo, Japan

[21] Appl. No.: 901,972

[22] Filed: Aug. 29, 1986

Related U.S. Application Data

[63] Continuation of Ser. No. 790,146, Oct. 22, 1985, abandoned.

[30] Foreign Application Priority Data

Oct. 26, 1984 [JP] Japan .................................. 59-225313

[51] Int. Cl.⁴ .............................................. A61B 1/04
[52] U.S. Cl. ............................................ 128/6; 358/98
[58] Field of Search .................... 128/4, 6; 358/98; 350/96.26

[56] References Cited

U.S. PATENT DOCUMENTS

| | | | |
|---|---|---|---|
| Re. 31,289 | 6/1983 | Moore et al. | 128/6 |
| Re. 31,290 | 6/1983 | Moore et al. | 128/6 |
| 4,146,019 | 3/1979 | Bass et al. | 128/6 |
| 4,281,646 | 8/1981 | Kinoshita | 128/6 |
| 4,491,865 | 1/1985 | Danna et al. | 358/98 |
| 4,509,507 | 4/1985 | Yabe | 128/4 |
| 4,562,831 | 1/1986 | Murakoshi et al. | 128/6 |
| 4,573,450 | 3/1986 | Arakawa | 128/6 |

Primary Examiner—William H. Grieb

[57] ABSTRACT

An endoscope apparatus includes an endoscope and a drive device connected to the endoscope and having a light source. In the distal-end surface of the insertion section of the endoscope, an observation window and an illumination window are provided. A solid-state image sensor is arranged in the distal-end portion of the insertion section to face the observation window. The sensor receives an optical image passing through the observation window, converts the image into electrical signals and transfers the signals in both vertical and horizontal directions. The sensor is so arranged that the vertical transferring direction defines an angle of about 50° to 90° with a line extending between the centers of the observation and illumination windows.

16 Claims, 21 Drawing Figures

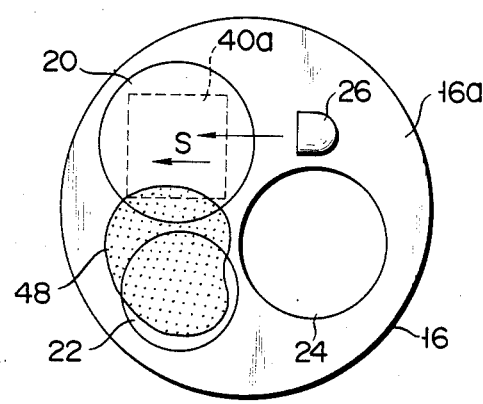
FIG. 2
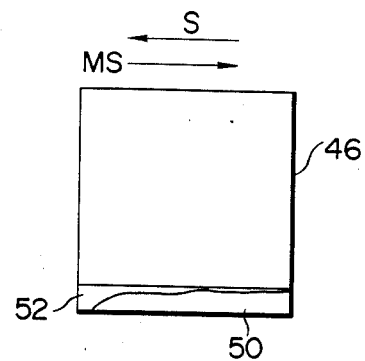
FIG. 3
FIG. 4
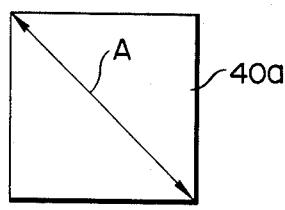
FIG. 5
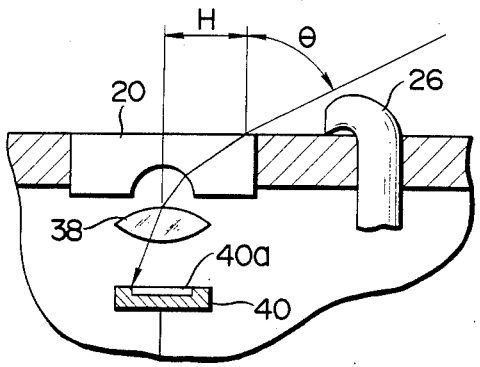
FIG. 6
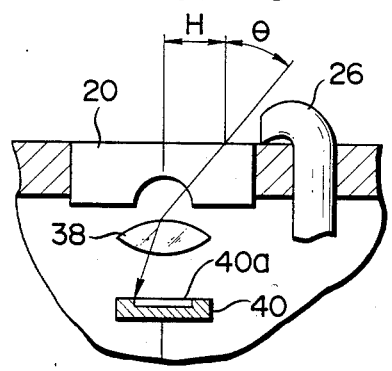
FIG. 7
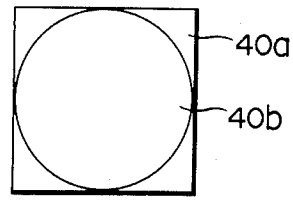

ENDOSCOPE APPARATUS HAVING NOZZLE ANGULARLY POSITIONED IMAGE SENSOR

This application is a continuation of application Ser. No. 790,146, filed Oct. 22,1985 abondoned.

BACKGROUND OF THE INVENTION

This invention relates to an endoscope apparatus, and, more particularly, to an endoscope apparatus for observing a body cavity by means of a solid-state image sensor.

Recently an endoscope designed to visibly photograph an observed spot by means of a solid-state image sensor has been proposed. Ordinarily, the solid-state image sensor converts an optical image brought to the light-receiving plane into electrical signals by scanning the optical image in a prescribed direction. The signals are treated by, for example, a video processing circuit and then displayed as a visible image on a monitor. If the above-mentioned type of solid-state image sensor is exposed to an intense light, then an electric charge overflows, causing blue streaks to run in the direction in which an image to be displayed on the monitor is scanned; namely, giving rise to the occurrence of the so-called blooming phenomenon.

Ordinarily, the plane of the distal aspect of an endoscope insertion section is provided with an observation window and illumination window juxtaposed with one another, and also with an air/water nozzle for cleaning the observation window. When water droplets are left, after washing, in a space defined between the observation and illumination windows, part of the light beams emitted from the illumination window directly enters into the observation window via the water droplets. In this case, some portions of the light-receiving plane of the solidstate image sensor are exposed to excessive amounts of light, giving rise to the aforementioned blooming phenomenon. In other words, when part of the monitor screen receives excessively large quantities of light, the entire scanning area, including those portions exposed to excessive illumination, gives evidence of the blooming phenomenon. This event leads to drawbacks such that the observation area on the monitor screen is too much reduced for satisfactory image pickup, and, moreover, that retention of the above-mentioned water droplets blurs whatever image is picked up.

SUMMARY OF THE INVENTION

This invention has been accomplished in view of the above-mentioned circumstances, and is intended to provide an endoscope apparatus capable of rendering an observation spot fully adapted for distinct observation.

To attain this object, the present invention provides an endoscope apparatus which comprises:
- an illumination window provided in the distal-end surface of the insertion section of the endoscope to irradiate light beams on an observation spot;
- an observation window built in the distal-end surface;
- a solid-state image sensor for converting an optical image projected through the observation window into electrical signals and transferring the signals in a horizontal as well as a vertical direction; and
- means for converting the electric signals into a visible image;
- and wherein said vertical transferring direction of the electrical signals is prescribed to define an angle of about 50 to 90 degrees with a line extending between the center of the observation window and that of the illumination window.

BRIEF DESCRIPTION OF THE DRAWINGS

FIGS. 1 to 7 illustrate an endoscope apparatus according to the first embodiment of the present invention; in which FIG. 1 is a schematic sectional view of the whole of the subject endoscope apparatus, FIG. 2 is a plan view of the distal-end surface of the insertion section, FIG. 3 is a plan view of a monitor screen, FIG. 4 is a plan view indicating the light-receiving area of the solid-state image sensor, FIGS. 5 and 6 are enlarged sectional views of the proximal aspect of the observation window, and FIG. 7 is a plan view of the light-receiving area of the solid-state image sensor;

FIG. 10 is a plan view of the distal-end surface of the insertion section of an endoscope apparatus according to a second embodiment of the invention;

FIGS. 11 and 12 show an endoscope apparatus according to a third embodiment of the invention; in which FIG. 11 is a schematic sectional view of the whole of the apparatus, and FIG. 12 is a plan view of the light-receiving area of the solid-state image sensor;

FIGS. 16 to 18 indicate an endoscope apparatus according to a seventh embodiment of the invention; in which FIG. 16 is a plan view of the distal-end surface of the insertion section, FIG. 17 is a plan view of the monitor screen, and FIG. 18 is a schematic diagram of the processing circuit;

FIGS. 19 and 20 represent an endoscope apparatus according to an eighth embodiment of the invention; in which FIG. 19 is a plan view of the distal-end surface of the insertion section, and FIG. 20 is a plan view of the monitor screen.

DETAILED DESCRIPTION OF THE PREFERRED EMBODIMENTS

The present invention will now be described with reference to the accompanying drawings.

Figure 1:
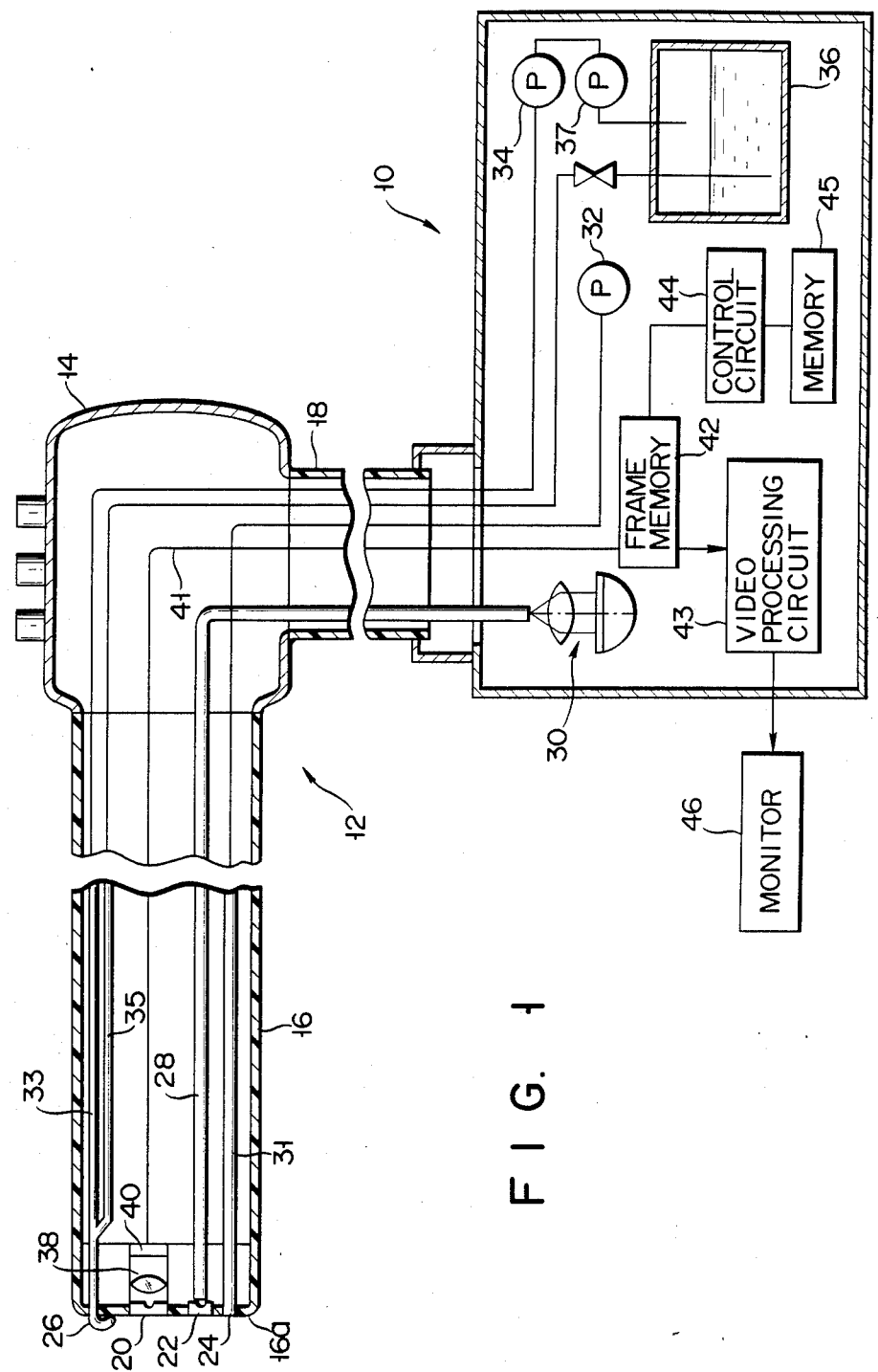

As shown in FIGS. 1 and 2, an endoscope apparatus comprises a drive unit 10 and an endoscope 12 connected to the drive unit 10. The endoscope 12 involves an operation section 14, a flexible insertion section 16 extending from the operation section, and a universal cord 18 extending from the operation section to the drive unit 10. The distal-end surface 16a of the insertion section 16 is provided with an observation window 20, illumination window 22 set vertically below the observation window, and suction port 24. The distal-end surface 16a is further fitted with an air/water nozzle 26 facing the observation window 20.

The illumination window 22 is connected to a light guide 28 which extends through the endoscope 12 up to the distal end of the universal cord 18. The light guide 28 conducts an illumination light issued from a light source 30 set in the drive unit 10 to the illumination window 22. The suction port 24 is connected to a suction pump 32, arranged in the drive unit 10, by means of a suction pipe 31 extending through the endoscope. The nozzle 26 is connected to an air pump 34, built in the drive unit 10, by means of an air supply pipe 33 extending through the endoscope, and also to a water pump 37 through a water supply pipe 35 running through the endoscope and a tank 36 received in the drive unit 10. After water is ejected from the nozzle 26 to the surface of the observation window 20, air is supplied to clean the observation window 20.

An objective lens 38 is provided on the inside of the observation window 20. A solid-state image sensor 40 is provided at the focal point of the objective lens 38. The sensor 40 converts an optical image projected through the observation window 20 and focused by the objective lens 38 into an electrical signals. The sensor 40 is connected to a frame memory 42, received in the drive unit 10, by means of a lead 41 extending through the endoscope 12. Connected to the memory 42 are a video-processing circuit 43 and a control circuit 44. A memory 45 is connected to the control circuit 44. The video-processing circuit 43 is connected to a monitor 46 composed of, for example, a cathode ray tube (CRT). The signals sent from the sensor 40 is processed by the video-processing circuit 43 and then the optical image is displayed on the monitor 46.

The solid-state image sensor 40 is made of a charge coupled device (CCD), and constructed by aligning a plurality of parallel transfer lines each of which is formed of a plurality of picture elements. As used herein, the lengthwise direction of the respective transfer lines is defined as the vertical transferring direction of the image sensor 40. A direction perpendicularly intersecting the transfer lines is referred to as the horizontal transferring direction.

As seen from FIG. 2, the sensor 40 is so arranged that the vertical transferring direction S defines an angle of 90° with a line extending between the center of the observation window 20 and that of the illumination window 22. In this case, the vertical transferring direction S is parallel with the horizontal scanning direction of the monitor 46, as indicated in FIG. 3. Ordinarily, the vertical transferring direction of the solid-state image sensor is set opposite to the vertical scanning direction of the cathode solenoid tube (CRT). When, therefore, the vertical transferring direction of the sensor 40 is rendered parallel with the horizontal scanning direction MS of the monitor 46, as shown in FIG. 3, the image appearing on the monitor has been rotated by an angle of 90°, if the electrical signals from the sensor are processed by the video-processing circuit 43 alone. According to the foregoing embodiment, therefore, the drive unit 10 is provided with the frame memory 42. The order in which signals are read out of the frame memory 42 is changed by the control circuit 44, thereby causing images displayed on the monitor 46 to be electrically rotated by 90°. The order in which signals are read out of the frame memory 42 is prestored in the memory 45.

As shown in FIG. 2, the solid-state image sensor 40 has a square light-receiving area 40a. The nozzle 26 is so set as to eject air or water in a direction perpendicular to one side of the light-receiving area. It is preferable to have the nozzle 26 positioned as close as possible to the observation window 20, because air can be conducted more forcefully and the insertion section 16 of the endoscope can be reduced in diameter. When, however, drawn too near the observation window 20, the nozzle 26 undesirably protrudes into the field of view. When, as shown in FIGS. 4 and 5, the nozzle 26 is set at a point on an extension of the diagonal line A of the light-receiving area 40a, the nozzle 26 cannot be drawn near the observation window 20, because the angle θ of the field of view and the hight H of the light rays along the diagonal line of the light-receiving area 40a are relatively large. For this reason, the foregoing embodiment is characterized in that, as shown in FIGS. 2 and 6, the nozzle 26 is set on a line perpendicularly intersecting one side of the square light-receiving area 40a. Since, in this case, the angle θ of the field of view and the hight H of the sensor 40 are smaller than in the above-mentioned case, the nozzle 26 can be drawn well near the observation window 20. When the light-receiving area 40a is rectangular, the nozzle is arranged to face the longer side of the area 40a.

The endoscope apparatus constructed as described above offers the following advantages. When the observation window 20 is cleaned by the air and water ejected through the nozzle 26, water droplets 48 are sometimes retained in a space defined between the observation window and illumination window 22. Consequently, part of the light beams emitted from the illumination window are directly projected onto the solid-state image sensor 40 through the water droplet 48. As a result, part of the light-receiving area 40a is exposed to an excessive amount of light. The screen of the monitor 46 is partly contaminated by an excessively illuminated portion 50, as shown in FIG. 3.

The endoscope apparatus embodying this invention, however, offers the following advantages with relation to its construction. The vertical transferring direction S of the sensor 40 perpendicularly intersects a line extending between the center of the observation window 20 and that of the illumination window 22. Consequently, the transfer lines of the sensor 40, which include the excessively illuminated picture elements, are represented only by several lines lying on the side of the illumination window 22. Therefore, an electrical charge overflowing the excessively illuminated picture elements is prevented from entering the other picture element lines. Consequently, that region 52 of the monitor screen 46 where the blooming phenomenon appears is very much limited. Thus even when a water droplet is left on the distal-end surface 16a of the insertion section of the endoscope, the area where the blooming phenomenon is generated is minimized, thereby broadening the visible region of the monitor screen 46.

The air/water nozzle 26 is directed along a line perpendicularly intersecting one side of the square light-receiving area 40a of the sensor 40, and consequently can be set near the observation window 20. Thus, air can be forcefully blown to the observation window 20 and water droplets retained between the observation window 20 and the illumination window 22 can be easily blown off. Further, the various elements lying on the distal-end surface 16a of the insertion section can be assembled in a compact form, thereby reducing the diameter of the insertion section 16.

In the foregoing embodiment, as shown in FIG. 7, signals from only those portions of the square light-receiving area 40a which lie within a circle 40b in the area 40a may be read out by controlling the order in which signals are read out of the frame memory 42 by means of the control circuit 44. In this case, it is possible to obtain an image having a uniform angle of view as measured in the vertical, horizontal and oblique directions.

In the foregoing embodiment, the solid-state image sensor 40 is so positioned as to cause the vertical transferring direction S to perpendicularly intersect a line extending between the center of the observation window 20 and that of the illumination window 22. However, this invention is not limited to this arrangement. The object can be attained provided the sensor 40 is so set that the vertical transferring direction defines an angle of about 50° to 90° with a line extending between the center of the observation window 20 and that of the illumination window 22.

Figure 8:
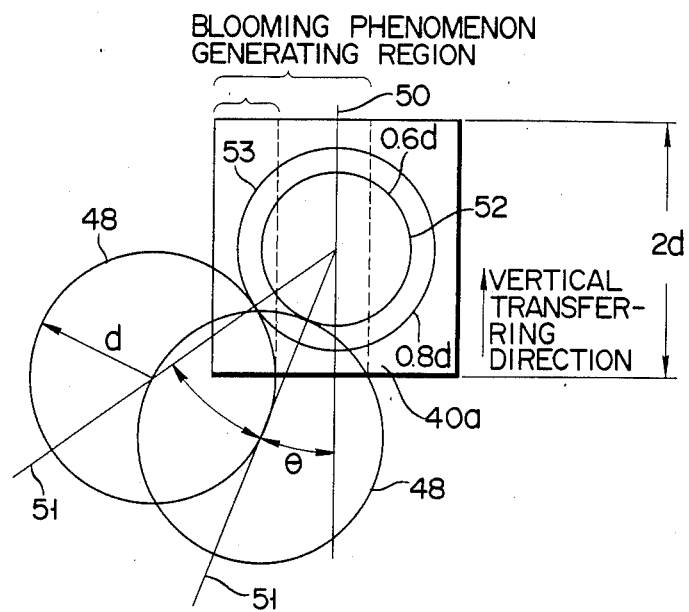
FIGS. 8 and 9 are a plan view and a characeristic diagram setting forth the shifted positions of a blooming-contaminated area related to the transferring direction of the solid-state image sensor and the positions of retained water droplets.
Figure 9:
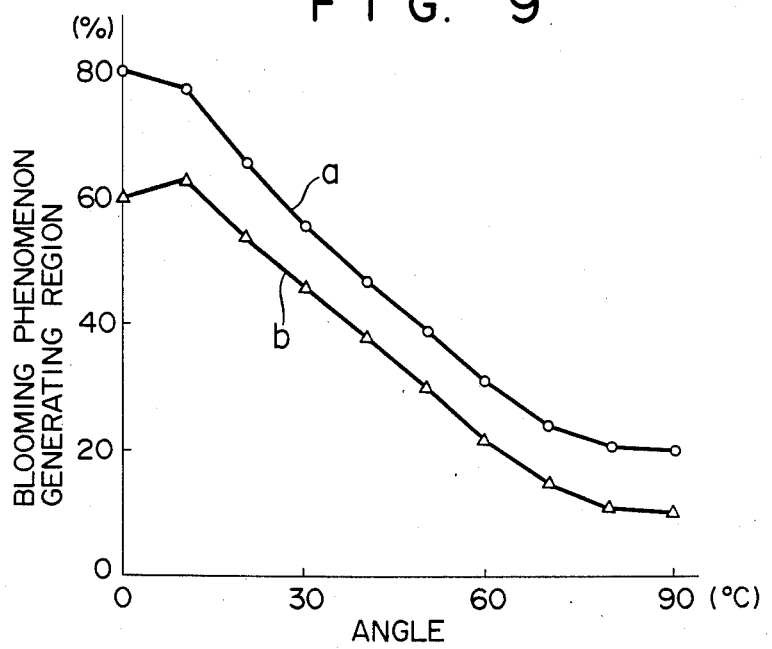

FIGS. 8 and 9 indicate the relationships between variations in the angle defined by the vertical transferring direction of the solid-state image sensor with a line extending between the center of the observation window 20 and that of the illumination window 22, and the shifting of the blooming phenomenon generating regions.

Referring to FIG. 8, the light-receiving area 40a of the sensor is shaped like a square, each side of which measures 2d, and the vertical transfer line of the sensor is indicated by a line 50. A line extending between the center of the observation window 20 and that of the illumination window 22 is indicated by a reference numeral 51. Assume that a water droplet 48 having a radius d is retained on the line 51. Circles 52 and 53 represent the positions of the water droplet 48 relative to the radial direction of the light-receiving area 40a. (The circle 52 is assumed to have a radius of 0.6d, and the circle 53 is assumed to have a radius of 0.8d.)

Referring to FIG. 9, line a indicates the relationship between the angle θ defined by the lines 50 and 51 and the ratio of the blooming phenomenon generating region to the whole light-receiving area when the water droplet 48 is retained on the circle 52 with respect to the light-receiving area 40a. Line b denotes the relationship between the angle θ and the ratio of the blooming phenomenon generating region when the water droplet 48 is retained on the circle 53 with respect to the light-receiving area 40a. Referring to line a, the ratio of the blooming phenomenon generating region to the light-receiving area 40a reaches a maximum of 80% when the angle θ stands at zero, and is reduced to approximately half that, or 40%, when the angle θ indicated is about 48°. Referring to line b, the ratio of the blooming phenomenon generating region reaches a maximum of 63% when the angle θ stands at about 10°, and is reduced to half that (that is, 31.5%) when the angle θ indicated is about 47°. As the result, if the angle θ defined by the lines 50 and 51 is prescribed to range between about 50° and 90°, the blooming phenomenon generating region can be reduced to half that which represents a region of maximum blooming phenomenon generation.

Figures 10, 11:
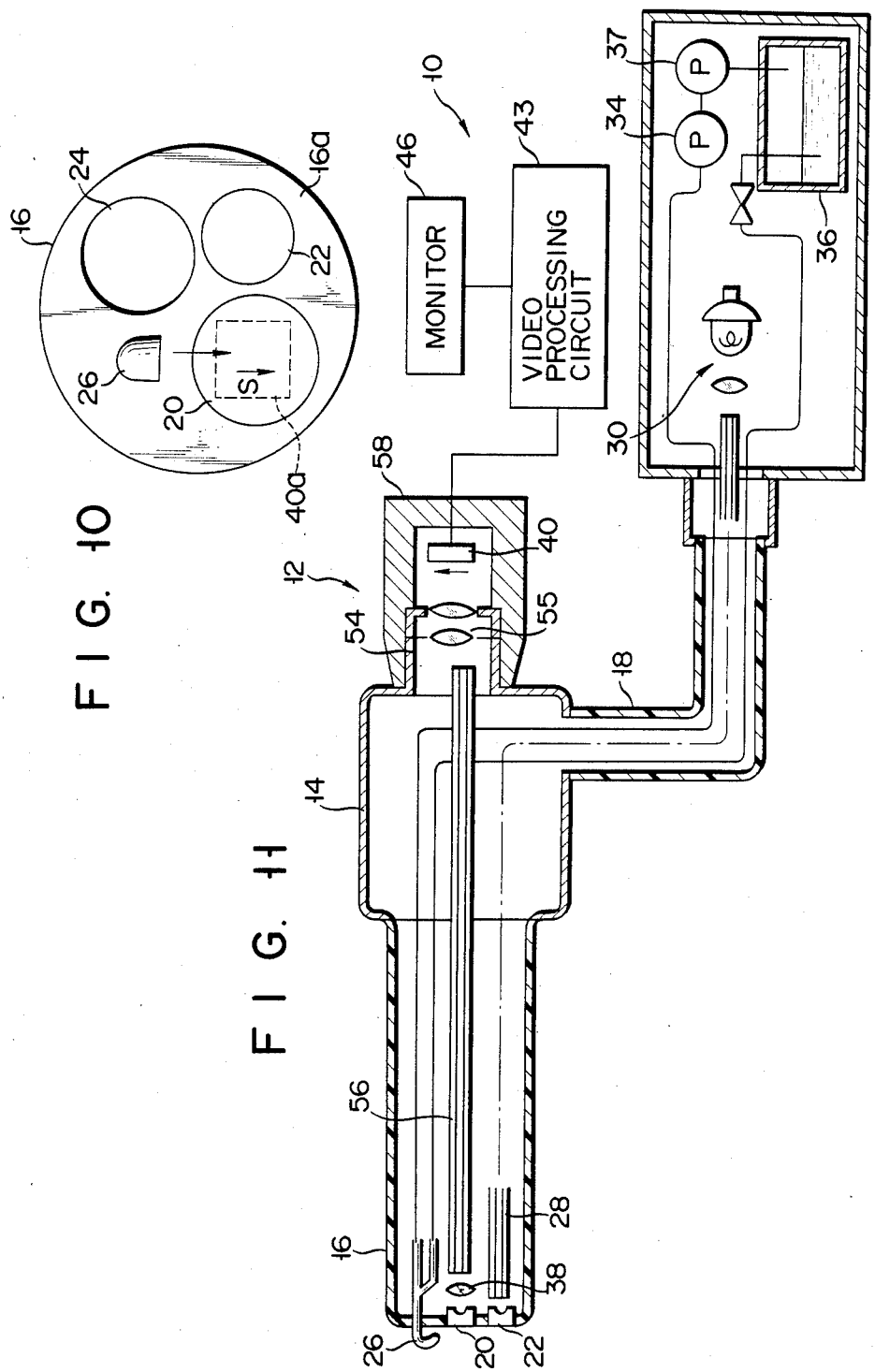

FIG. 10 indicates an endoscope apparatus according to a second embodiment of this invention. In this embodiment, the observation window 20 and illumination window 22 are aligned in the horizontal direction. The air/water nozzle 26 is set above the observation window 20. The vertical transferring direction S of the solid-state image sensor 40 perpendicularly intersects a line extending between the center of the observation window 20 and that of the illumination window 22.

With the second embodiment, it is unnecessary to provide a frame memory 42 thereby to change the order in which signals are read out of the sensor 40.

Figure 12:
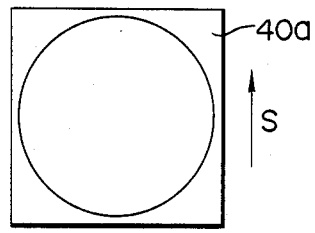

FIG. 11 illustrates an endoscope apparatus according to a third embodiment. In this third embodiment, a solid-state image sensor occupies a different position from that in the foregoing embodiments. Namely, according to this embodiment, the endoscope 12 comprises an eyepiece section 54 protruding from the operation section 14. The eyepiece section 54 is provided with an eyepiece 55. The objective lens 38 facing the observation window 20 and the eyepiece 55 are optically connected by means of an image guide 56 extending through the endoscope 12. Therefore, an optical image projected into the observation window 20 can be observed by the naked eye through the eyepiece section 54. A camera 58 receiving the solid-state image sensor 40 is detachably fitted to the eyepiece section 54. The sensor 40 is supplied with an optical image sent forth through the image guide 56 and eyepiece 55, and converts the image into an electrical signals which, in turn, are delivered to the video-processing circuit 43. The image guide 56 has a circular cross section, and consequently the light-receiving area 40a of the sensor 40 receives a circular optical image as shown in FIG. 12. The vertical transferring section S of the sensor 40 perpendicularly intersects a line extending between the center of the observation window 20 and that of the illumination window 22. In FIG. 11, parts the same as those of FIG. 1 are denoted by the same numerals, and description thereof is omitted.

Figure 13:
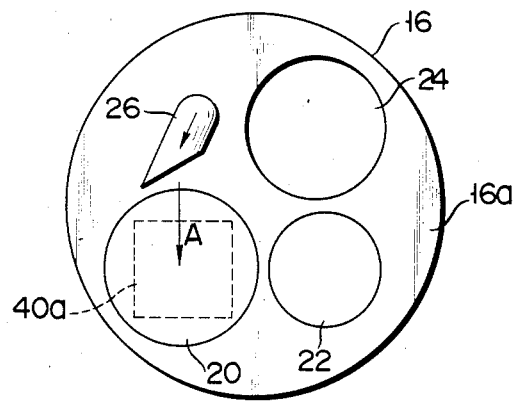
FIG. 13 is a plan view of the distal-end surface of the insertion section of an endoscope apparatus according to a fourth embodiment of the invention.

According to the fourth embodiment of the invention shown in FIG. 13, the ejection end of the air/water nozzle 26 is obliquely cut, thereby enabling air and water ejected through the nozzle to cover a broader area.

Figure 14:
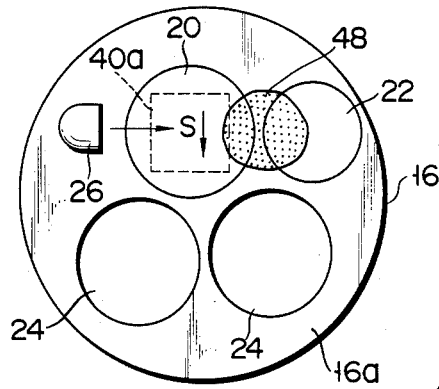
FIG. 14 is a plan view of the distal-end surface of the insertion section of an endoscope apparatus according to a fifth embodiment of the invention.

According to the fifth embodiment of the invention indicated in FIG. 14, the illumination window 22, observation window 20 and air/water nozzle 26 are horizontally aligned. The observation window 20 is interposed between the nozzle 26 and illumination window 22. The nozzle 26 faces the observation window 20 and illumination window 22. Consequently, after the ejection of air and water through the nozzle 26, a water droplet 48 is unlikely to be retained between the observation window 20 and illumination window 22, thereby reducing the generation of the blooming phenomenon.

Figure 15:
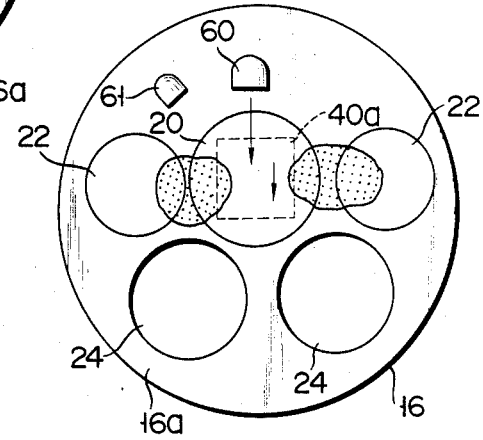
FIG. 15 is a plan view of the distal-end surface of the insertion section of an endoscope apparatus according to a sixth embodiment of the invention.

According to the sixth embodiment of the invention shown in FIG. 15, illumination windows 22 are provided in the horizontal plane on both sides of the observation window 20. An air nozzle 60 and water nozzle 61 are individually provided. The air nozzle 60 is set above the observation window 20, namely on a line perpendicularly intersecting one side of the square light-receiving area 40a of the sensor 40 and in the proximity of the observation window 20 in order to effectively blow water off of the observation window. The water nozzle 61 is positioned on a diagonal line of the square light-receiving area 40a, because the water nozzle 61, though somewhat removed from the observation window 20, has sufficient pressure to enable the water to reach and effectively clean the observation window 20.

Figure 16:
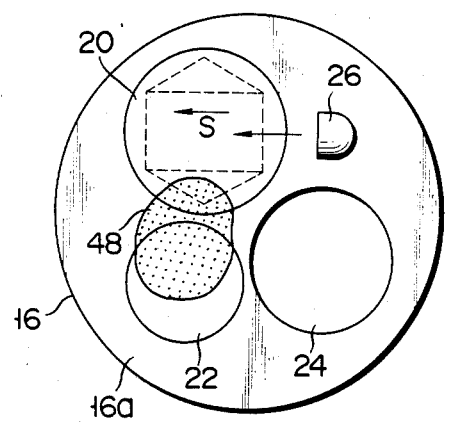
Figure 17:
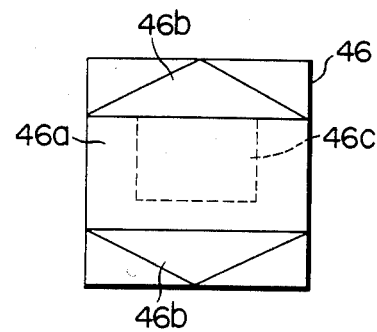
Figure 18:
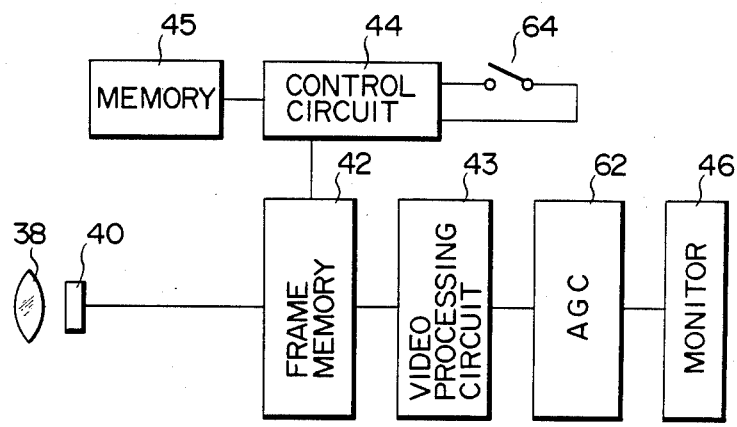

FIGS. 16 to 18 indicate an endoscope apparatus according to a seventh embodiment of this invention. With this seventh embodiment, the display area of the monitor 46 is divided into plural sections, thereby enabling any desired divided display section to be selected according to the condition of the observation window 20. As illustrated in FIG. 17, the screen of the monitor 46 is composed of a first display area 46a occupying the central position and a second display area 46b divided into two sections lying above and below the first display area 46a. Thus it is possible to use either the first display area 46a alone, or both first and second display areas 46a and 46b at the same time, as need arises. For selection of the display areas 46a and 46b, the drive circuit comprises a frame memory 42 connected to the sensor 40, and a video-processing circuit 43 and a control circuit 44 both connected to the frame memory. The video-processing circuit 43 is connected to a monitor 46 through a autmatic gain control circuit (AGC) 62. The control circuit 44 is connected to a memory 45 and changeover switch 64. The shifting of the plural display areas of the monitor 46 is effected by changing the operation mode of the changeover switch 64.

The liquid repellency of the observation window 20 changes during even one medical examination. Namely, when the surface of the observation window 20 is wiped clean, the surface allows for the high volatility of a liquid and exhibits good liquid repellency. When, however, the insertion section of the endoscope is taken into the coeliac cavity, saliva, for example, attaches to the observation window, resulting in an increase in the hidrophile property of the surface of the observation window 20. Particularly when contaminated by a gastric juice, the surface of the observation window 20 noticeably increases in hidrophile property. When the surface of the observation window 20 is cleaned, that portion of the observation window 20 which extends in the air-conducting direction of the air/water nozzle 26 can be washed relatively well and indicates a satisfactory liquid repellency. However, the surroundings of said portion indicate low liquid repellency. Once the gastric juice settles on the surface of the observation window 20, the liquid repellency falls noticeably. Further as the time of a medical examination is extended, the surface of the observation window increases in hidrophile property. Or, in other cases, the calcium component of running water attaches on the surface of the window 20 and decreases its liquid repellency.

For this reason, the seventh embodiment (FIGS. 16 to 18) causes the display areas of the monitor 46 to be selected in accordance with the physical conditions of the surface of the observation window 20. Namely, when the surface of the observation window 20 has a good liquid repellency, the first and second display areas 46a and 46b are used to ensure the broadest possible observation range. Conversely, when the surface of the observation window 20 falls in liquid repellency, namely, when a water droplet 48 is retained between the observation window 20 and illumination window 22, the first display area 46a alone is used. When the display areas of the monitor 46 are properly selected in accordance with the physical condition of the surface of the observation window 20, as described above, it is possible to eliminate an desired blooming phenomenon generating region from the monitor screen, thereby facilitating observation.

Referring to the above-mentioned seventh embodiment, it is possible, as shown by broken lines in FIG. 17, to control the light-measuring range 46c to be apart from the illumination window 22. This process prevents a water droplet retained between the observation window 20 and illumination window 22 from exerting a harmful effect, thereby enabling the observation region of the observation window 20 to be properly illuminated.

Figure 19:
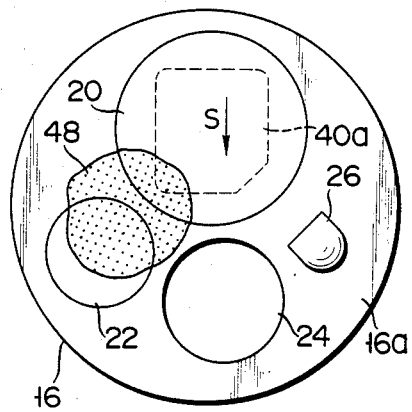
Figure 20:
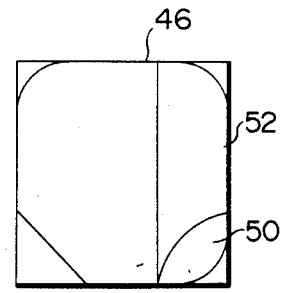

Description may now be given, with reference to FIGS. 19 and 20, of an endoscope apparatus according to an eighth embodiment of this invention. In this embodiment, the solid-state image sensor 40 is so positioned that its vertical scanning direction S defines an angle of about 50°, with a line extending between the center of the observation window 20 and that of the illumination window 22. The nozzle 26 is set on a diagonal line of the light-receiving area 40a of the sensor 40. The air-liquid transmitting direction of the nozzle 26 perpendicularly intersects a line extending between the center of the observation window 20 and that of the illumnation window 22. The corner section of that side of the light-receiving area 40a which faces the nozzle 26 is cut obliquely in order to prevent the nozzle 26 from entering the field of view. Further, as illustrated in FIG. 20, the display area of the monitor 46 is so designed as to divert light to the left side of FIG. 20 in order to eliminate the blooming phenomenon generating region 52 from the monitor screen.

The parts of FIGS. 13 to 16 and 19, being the same as those of FIG. 2, are denoted by the same numerals, and description thereof is omitted.

Figure 21:
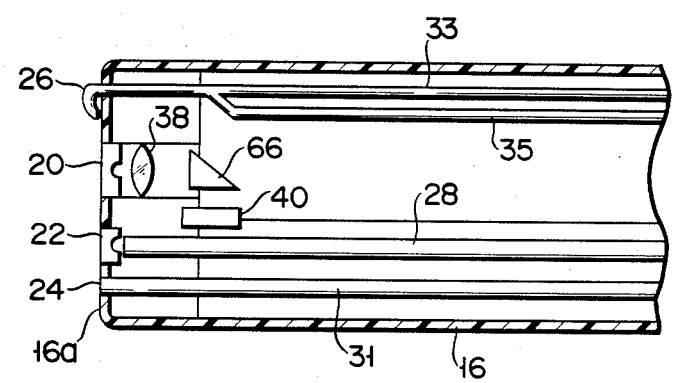
FIG. 21 is a sectional view of the insertion section of an endoscope apparatus according to an ninth embodiment of the invention.

In the above embodiments, the solid-state image sensor is arranged to face the objective lens. However, the sensor may be arranged as shown in FIG. 21. In this case, the optical image passing through the objective lens 38 is projected onto the sensor through a prism 66.

What is claimed is:

1. An endoscope apparatus for observing any desired spot in the coeliac cavity, which comprises:
    an endoscope including an operation section, a flexible insertion section extending from the operation section for insertion into the coeliac cavity, and a universal cord protruding from the operation section;
    a light source device connected to the universal cord;
    a drive device;
    said endoscope including an illumination window set in the distal-end surface of the insertion section, a light guide conducting a light from the light source device to the illumination window to illuminate the observation spot through the illumination window, an observation window set in the distal-end surface of the insertion section, a solid-state image sensor having a light receiving surface, for receiving an optical image passing through the observation window, converting the image into electrical signals, and transferring the signals in both vertical and horizontal directions, and a nozzle set in the distal-end surface of the insertion section to transmit air and water to the observation window for cleaning;
    said drive device including a video-processing circuit for converting electrical signals issued from the sensor into image signals; and a monitor for displaying an image in accordance with the image signals from the drive device;
    and wherein the vertical transferring direction of the sensor defines an angle of about 50° to 90° with an imaginary line which extends between the center of said observation window and that of the illumination window and which is projected on the light receiving surface of the sensor.

2. The endoscope apparatus according to claim 1, wherein the air/water transmitting direction of said nozzle is set in parallel with the vertical transferring direction of the solid-state image sensor.

3. The endoscope apparatus according to claim 2, wherein said solid-state image sensor has a rectangular light-receiving area, and the vertical transferring direction is set in parallel with one side of the light-receiving area.

4. The endoscope apparatus according to claim 3, wherein the vertical transferring direction of said solid-state image sensor perpendicularly intersects a line extending between the center of the observation window and that of the illumination window.

5. The endoscope apparatus according to claim 1, wherein said nozzle is set on the side of the illumination window opposite the observation window, and the air/water transmitting direction of the nozzle perpendicularly intersects the vertical transferring direction.

6. The endoscope apparatus according to claim 5, wherein the vertical transferring direction of said solid-state image sensor perpendicularly intersects a line extending between the center of the observation window and that of the illumination window.

7. The endoscope apparatus according to claim 1, wherein said drive device includes image-processing means for processing the electrical signals issued from the sensor.

8. The endoscope apparatus according to claim 7, wherein the vertical transferring direction of said solid-state image sensor is set horizontal on the distal-end surface of the insertion section.

9. The endoscope apparatus according to claim 7, wherein the vertical transferring direction of said solid-state image sensor is set vertical on the distal-end surface of the insertion section.

10. The endoscope apparatus according to claim 7, wherein said image-processing means includes a frame memory connected between the video-processing circuit and the solid-state image sensor to store electrical signals issued from the sensor, a control circuit for controlling the order in which signals are read out of the frame memory, and a memory for storing the controlled order in which the signals are read out.

11. The endoscope apparatus according to claim 7, wherein said monitor includes a screen divided into a plurality of display areas, and said image-processing means involves means for selectively shifting the display areas.

12. The endoscope apparatus according to claim 1, wherein said solid-state image sensor is arranged in the distal-end portion of the insertion section to face the observation window, and said endoscope includes an objective lens which is interposed between the observation window and sensor to focus an optical image projected through the observation window on the sensor.

13. The endoscope apparatus according to claim 1, wherein said endoscope includes an objective lens which is arranged in the distal-end portion of the insertion section to face the observation window for focussing an optical image projected through the observation window, an eyepiece section involving an eyepiece and arranged in the operation section, and an image guide for conducting an optical image projected through the observation window to the eyepiece; said solid-state image sensor being detachably fitted to the eyepiece section to face the eyepiece.

14. The endoscope apparatus according to claim 1, wherein said solid-state image sensor is formed of a charge coupled device.

15. The endoscope apparatus according to claim 1, wherein said solid-state image sensor is arranged so that the light receiving surface is parallel to the observation window.

16. The endoscope apparatus according to claim 1, wherein said solid-state image sensor is arranged so that the light receiving surface is perpendicular to the observation window.

* * * * *